United States Patent [19]
Yifrach et al.

[11] Patent Number: 5,118,181
[45] Date of Patent: Jun. 2, 1992

[54] METHOD AND APPARATUS FOR IDENTIFYING GEMSTONES, PARTICULARLY DIAMONDS

[75] Inventors: Aharon Yifrach, Ashkelon; Uri Neta, Haifa, both of Israel

[73] Assignee: Wellborn Ltd., Ramat Gan, Israel

[21] Appl. No.: 599,923

[22] Filed: Oct. 19, 1990

[30] Foreign Application Priority Data

Oct. 27, 1989 [IL] Israel .................................. 92133

[51] Int. Cl.⁵ ...................... G01N 21/64; G01N 21/87
[52] U.S. Cl. ................................. 356/30; 250/461.1
[58] Field of Search .............. 356/30, 317, 318, 417; 250/458.1, 459.1, 461.1, 461.2

[56] References Cited

U.S. PATENT DOCUMENTS 4,394,580 7/1983 Gielisse .................................. 356/30

FOREIGN PATENT DOCUMENTS 22215041 9/1989 United Kingdom .................. 356/30

Primary Examiner—F. L. Evans
Attorney, Agent, or Firm—Benjamin J. Barish

[57] ABSTRACT

A method of identifying a gemstone, particularly a diamond by: exciting the gemstone to cause it to emit luminescence radiation according to a luminescence spectrum unique to the respective gemstone, in which the luminescence intensity uniquely varies as a function of wavelength; measuring the level of the luminescence radiation at a plurality of preselected wavelengths of its luminescence spectrum; and utilizing the levels of the luminescence radiation at the preselected wavelenths to identify the respective gemstone and to distinguish it from other gemstones.

23 Claims, 2 Drawing Sheets

METHOD AND APPARATUS FOR IDENTIFYING GEMSTONES, PARTICULARLY DIAMONDS

FIELD AND BACKGROUND OF THE INVENTION

The present invention relates to a method and apparatus for identifying gemstones, particularly diamonds, enabling each diamond to be distinguished from other diamonds.

Gemstones in general, and diamonds in particular, are commonly classified according to various properties, including weight, colour and purity, which properties greatly affect the value of the diamond. An expert gemologist is usually required to evaluate these properties in order to determine the value of the diamond and also to identify and distinguish one particular diamond from all other diamonds. A need therefore exists for a method and apparatus to identify gemstones in general, and diamonds in particular, enabling even a non-expert to quickly and positively identify any particular gemstone and to distinguish it from others.

A number of methods have been proposed in the past for identifying gemstones, particularly diamonds. Among these known methods are those based on: reflection techniques, as illustrated in U.S. Pat. Nos. 3,740,142 and 3,947,120; geometric scattering techniques, as illustrated in U.S. Pat. No. 4,012,141; Raman refraction techniques, as illustrated in U.S. Pat. No. 4,799,786; ion implantation techniques, as illustrated in U.S. Pat. Nos. 4,200,506 and 4,316,385; laser microengraving techniques, as illustrated in U.S. Pat. No. 4,467,172 and Israel Patent 64274; and x-ray techniques, as illustrated in U.S. Pat. No. 4,125,770. However, none of these known techniques has yet found widespread use, primarily because of one or more of the following drawbacks: the high cost and cumbersome procedures required for identifying the diamonds; the lack of reproducibility enabling the same identification results to be obtained using various types of identification apparatus and working conditions; and/or the inability of identifying the diamond while held in a setting.

OBJECT AND BRIEF SUMMARY OF THE INVENTION

An object of the present invention is to provide a new method and apparatus for identifying gemstones, and particularly diamonds, having advantages over the previously-known techniques in one or more of the above respects.

The present invention provides a method of identifying a gemstone, particularly a diamond, comprising: exciting the gemstone to cause it to emit luminescence radiation according to a luminescence spectrum unique to the respective gemstone, in which the luminescence intensity uniquely varies as a function of wavelength; uniformly distributing the luminscence radiation by a light-diffusion surface; measuring the level of the uniformly distributed luminescence radiation at each of a plurality of preselected wavelengths (or frequencies) of the luminescence spectrum; and utilizing the levels of the luminescence radiation at said preselected wavelengths to identify the respective gemstone and to distinguish it from other gemstones.

Luminescence is the visible glow of light . produced in certain substances when excited by rubbing, scratching, chemically changing, or irradiating the substance, e.g., by sunlight, other sources of ultraviolet or infrared rays, cathode rays, and x-rays. Luminescence includes both fluorescence (the visible glow of light during the exciting of the substance by irradiation), and also phosphorence (the afterglow produced on removal of the excitation source). Gemologists frequently observe luminescence of a diamond under ultraviolet light as a positive test for a diamond and also as one means for determining its purity.

In the present invention, the luminescence of the gemstone is utilized for identifying the gemstone and for distinguishing it from other gemstones, by measuring the level of the luminescence at preselected wavelengths (or frequencies) of its luminescence spectrum, to provide a series of values, each representing one of the preselected wavelengths. These values are unique for each gemstone as they depend on the structure and composition of the gemstone. Therefore, they may be used as a "fingerprint" for positively identifying the gemstone and for distinguishing it from all other gemstones. Preferably, the light intensity of the gemstone is measured at least at six points of its luminescence spectrum to provide a series of at least six values. These series of values may be converted to a single identification number identifying the respective diamond.

In the preferred embodiment of the invention described below, the gemstone is excited by exposing it to a source of non-visible radiation, preferably ultraviolet or infrared radiation. This simplifies measuring the luminescence radiation produced as a result of the excitation since it better enables measuring the luminescence radiation without interference by the excitation radiation used for exciting the gemstone to luminescence.

In the described preferred embodiment, the luminescence radiation is uniformly distributed by a light-diffusing surface before it is measured. Best results have been obtained where the light-diffusing surface is an integrating sphere, such as one consisting of two hemispheres that are mated together to form a spherical cavity with the inner surface of the sphere coated with a high-reflectance diffusing coating. Thus, radiation introduced into the sphere and incident upon the coated surface is reflected in random directions, thereby producing a very uniform distribution of the radiation which is directly proportional to the total amount of light introduced into the sphere. The intensity (flux density) of such light within the sphere at different frequency points of the spectrum may be measured by a plurality of photodetectors mounted at different ports in the sphere wall, each photodetector being sensitive to a different frequency band of the spectrum.

In the described preferred embodiment, the luminescence radiation is measured by detectors via pinholes through the light-diffusing surface, which surface includes a baffle shielding its respective pinhole and detector from direct exposure to the source of non-visible radiation.

The invention also provides apparatus for identifying a gemstone, particularly a diamond, in accordance with the above method.

The above method and apparatus thus enable gemstones to be identified and distinguished from other gemstones by using relatively low cost equipment and relatively simple procedures. The above method and apparatus have been found to exhibit a high degree of reproducibility even when the procedure is performed by non-experts and under varying conditions. In addition, the method and apparatus may be used for identifying gemstones while still held in their settings, and do not require removal of the gemstone from its setting, thereby further simplifying the procedure as compared to some of the previously-known procedures.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
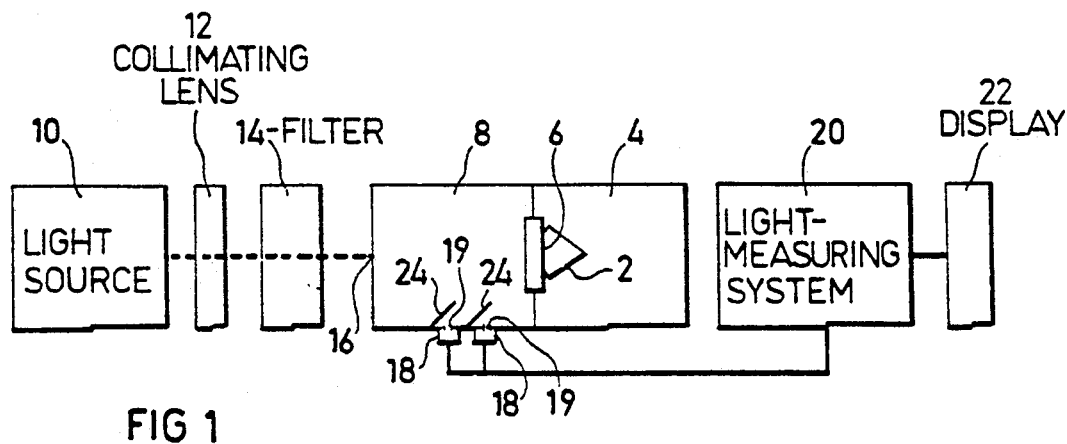
FIG. 1 is a diagram schematically illustrating one form of apparatus constructed in accordance with the present invention for identifying gemstones, particularly diamonds.

In the diagram of FIG. 1, the gemstone 2, e.g., a diamond, to be identified is mounted within an enclosure 4 such that the flat table of the diamond is exposed via a window 6 communicating with the inside of another enclosure 8. The diamond 2 is exposed to an intense light source 10 via a collimating lens 12, a filter 14, and an inlet opening 16 in the front wall of enclosure 8. Light source 10 excites the diamond 2 to luminescence, causing it to radiate according to a luminescence spectrum unique to the diamond. The luminescence intensity produced by thus exciting the diamond, is detected by a plurality of light detectors 18 communicating with the inside of enclosure 8. The light intensity is measured and processed by a light-measuring system represented by block 20 in FIG. 1, and is displayed in a display device 22.

The light source 10 is preferably a source of non-visible radiation, such as ultraviolet light or infrared light. It is filtered by filter 14 to remove the visible radiation, and is collimated by the optical system 12 to produce parallel rays directed towards inlet opening 16 in enclosure 8. The parallel light rays enter inlet opening 16 and pass through window 6 into the table of the diamond 2, thereby exciting the complete diamond to luminescence.

Enclosure 4 enclosing the diamond 2 includes a highly-reflective inner surface which reflects the luminescence radiation back through window 6 into enclosure 8. The latter enclosure is formed with a light-diffusive surface having a high reflectance so as to uniformly distribute the luminescence radiation within the enclosure. Detectors 18 have different spectral responses, i.e., they are sensitive to different frequency bands of the luminescence spectrum. There are as many detectors 18 as points of the luminescence spectrum to be sampled, preferably at least six; and each communicates with the interior of enclosure 8 via an opening 19.

The light-measuring system 20, to which the detectors 18 are connected, thus measure the level of the luminescence radiation within enclosure 8 at preselected sample points of the light spectrum. The resulting measurements are processed and displayed in display 22 (e.g., a visual display, printer or recorder), and thereby serve as an identification of the examined diamond 2.

Window 16 receiving the exciting radiation, as well as the openings 19 through which the detectors 18 are exposed to the luminescence radiation, are preferably pinholes so as to minimize the disturbance of these openings in the uniformity of the distribution of the luminescence radiation within enclosure 8. Opening 19 of each detector 18 is shielded by a baffle, as indicated schematically at 24, from direct exposure to the exciting radiation from the light source 10 and from direct luminescence radiation, so that the light detected by it will consist only of the visible indirect luminescence radiation and will be substantially free of the non-visible exciting radiation.

Figure 2:
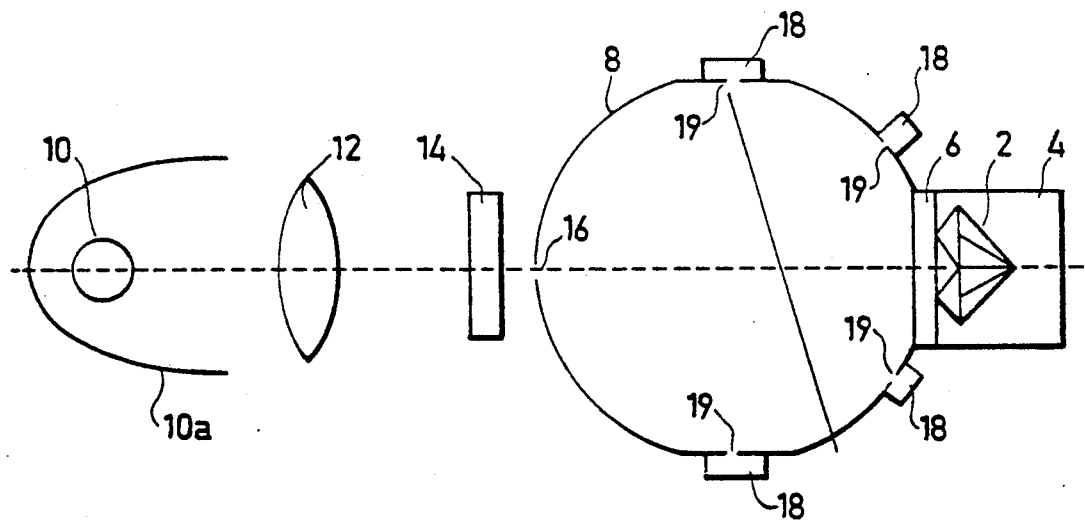
FIG. 2 diagrammatically illustrates one particular implementation of the optical system in the apparatus of FIG. 1.

FIG. 2 more particularly illustrates one implementation of the optical portion of the apparatus illustrated in FIG. 1.

The high-intensity ultraviolet light source 10 includes a parabolic reflector 10a for directing the light first through collimating lens 12 and then through filter 14 which removes the visible parts of the light. Enclosure 8 is an integrating sphere, and its window 6 is a quartz window which is transparent to both ultraviolet and visible light.

The excitation light enters the table of the gemstone, and the luminescence created by this excitation of the gemstone is radiated out of the gemstone in all directions. The reflecting surface of enclosure 4 enclosing the gemstone reflects the radiation back through the quartz window 6 so that substantially all the luminescence radiation enters the integrating sphere 8. The high-reflectance light-diffusing coating of integrating sphere 8 uniformly distributes the luminescence radiation within it to produce a spatially integrated radiation distribution. Thus, the radiation spectrum within the integrating sphere 8 is completely uniform, such that it can be detected in each spot on the sphere surface.

The unique luminescence spectrum produced for the respective gemstone is detected by the plurality of detectors 18 each of which has a different spectral response so as to be sensitive to a different frequency or wavelength while blind to the exciting ultraviolet radiation. As mentioned earlier, each detector 18 communicates with the interior of the integrating sphere 8 via pinhole 19 so as not to disturb the uniformity of the distribution of the luminescence within the sphere, and its pinhole includes a baffle 24 so as to be free from direct exposure to the ultraviolet light from excitation source 10.

Figure 3:
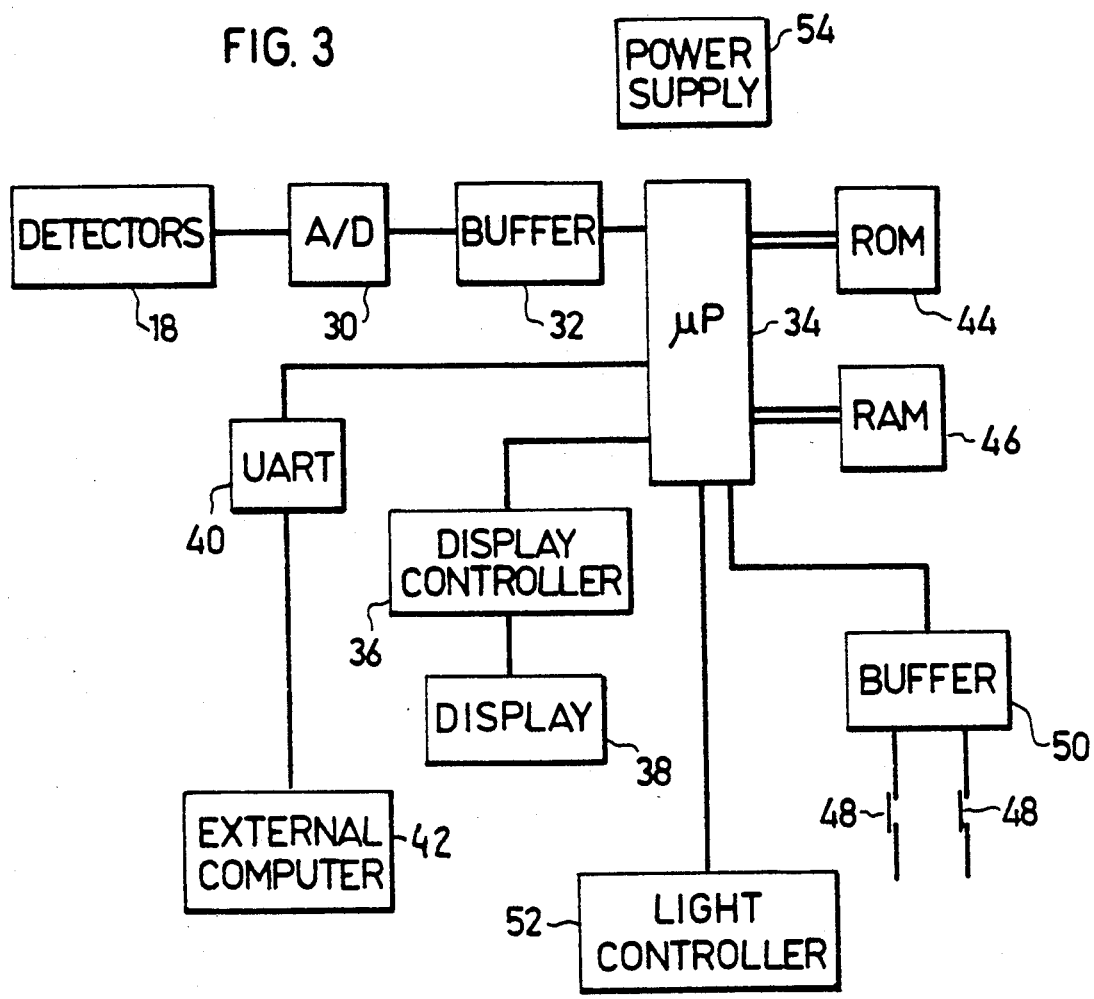
FIG. 3 is a block diagram of one form of light-measuring system which may be used in the apparatus of FIGS. 1 and 2.

FIG. 3 illustrates one example of a light-measuring system which may be used as the unit identified by 20 in FIG. 1 for measuring and processing the luminescence radiation, detected by the detectors 18.

The electrical signals outputted from the detectors 18 may be in the form of analog DC or AC voltages proportional to the detected radiation intensity. These outputs are fed to an analogue-to-digital converter 30 which produces a digital output fed via a buffer 32 to the I/O port of a microprocessor 34 which produces therefrom a measurement of frequency (or wavelength).

Microprocessor 34 processes this information and outputs it via a display controller 36 to a display 38. It may also output this information via a UART 40 to an external computer 42 for further processing.

Microprocessor 34 is controlled by a programme stored in a ROM (read only memory) unit 44 and also includes a RAM (random access memory) unit 46 for storing and retrieving data during its operation. The operating keys of microprocessor 34 for controlling its operation (e.g., "Test" and "Read" operations) are schematically shown at 48, and are connected to the microprocessor through a buffer 50.

Microprocessor 34 may also be used for controlling the ultraviolet light source (10, FIGS. 1 and 2) via a controller 52. The power supply for the system is schematically illustrated in FIG. 3 by block 54.

Figure 4:
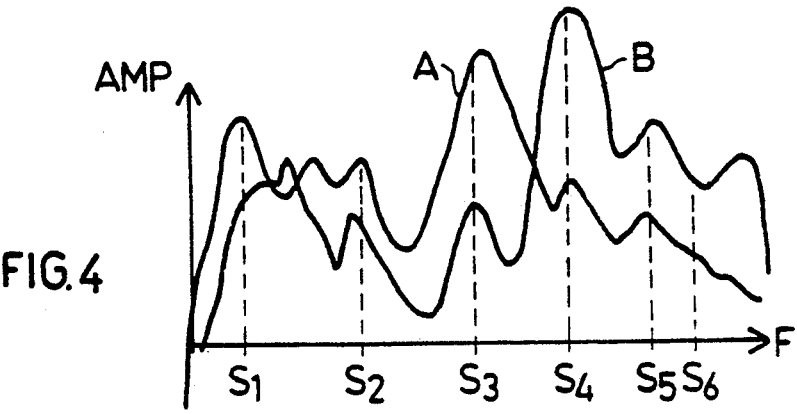
FIG. 4 illustrates the luminescence spectra of two diamonds and how these spectra may be used for identifying the respective diamonds and for distinguishing them from all other diamonds.

FIG. 4 illustrates two luminescence spectra A, B, of two different gemstones, showing how the intensity of the produced luminescence uniquely varies as a function of the frequency (or wavelength). Thus, by measuring the intensity of the luminescence radiation at preselected frequencies (or wavelengths), the gemstone may be identified and distinguished from all other gemstones. Preferably, the luminescence radiation is measured at least at six frequencies, indicated at S1–S6 in FIG. 4, but a larger (or smaller) number of frequencies may be used if desired. Since the described system includes a plurality of detectors each having a different spectral response, the system may use six such detectors, one for each frequency, so that the outputs of the detectors will indicate the intensity of luminescence radiation at the respective frequency. If desired, the six-value output can be used as the identifying "fingerprint", or can be converted to a single identification number identifying the respective gemstone and distinguishing it from all other gemstones.

It will thus be seen that the described method and apparatus can be used for identifying gemstones, particularly diamonds, in a convenient, relatively-low cost, and reproducible manner. It will also be seen that the method and apparatus do not require that the gemstone be removed from its setting in order to enable it to be identified, thereby further increasing its convenience.

While the invention has been described with respect to one preferred embodiment, it will be appreciated that many variations may be made. For example, the luminescence radiation may be focused on the detectors. Also, instead of using a filter set having different spectral responses, there may be used one detector with a circular variable filter (CVF). Further, the excitation light may be directed from all directions on the gemstone.

Many other variations, modifications and applications of the invention will be apparent.

What is claimed is:

1. A method of identifying a gemstone, particularly a diamond, comprising:
    exciting the gemstone to cause it to emit luminescence radiation according to a luminescence spectrum unique to the respective gemstone, in which the luminescence intensity uniquely varies as a function of wavelength;
    uniformly distributing said luminescence radiation by a light-diffusing surface;
    measuring the level of the uniformly-distributed luminescence radiation at each of a plurality of preselected wavelengths of its luminescence spectrum;
    and utilizing the levels of the luminescence radiation at said preselected wavelengths to identify the respective gemstone and to distinguish it from other gemstones.

2. The method according to claim 1, wherein the luminescence radiation of the gemstone is measured at least at six preselected wavelengths of its luminescence spectrum.

3. The method according to claim 1, wherein the luminescence radiation of the gemstone is measured by a plurality of detectors each sensitive to a different frequency band of the luminescence spectrum.

4. The method according to claim 1, wherein said gemstone is excited by exposing it to a source of non-visible radiation.

5. The method according to claim 4, wherein said light-diffusing surface is in an integrating sphere.

6. The method according to claim 5, wherein the luminescence radiation is measured by at least one detector via a pinhole through said light-diffusing surface.

7. The method according to claim 6, wherein said light-diffusing surface includes a baffle shielding said pinhole and detector from direct exposure to the source of non-visible radiation.

8. The method according to claim 6, wherein the luminescence radiation is measured by a plurality of detectors each via a pinhole through the light-diffusing surface, said light-diffusing surface including a baffle for each pinhole shielding the pinhole and its detector from direct exposure to the source of non-visible radiation.

9. The method according to claim 4, wherein said gemstone is excited by directing radiation from said source of non-visible radiation through the table of the gemstone while the remainder of gemstone is enclosed by an enclosure having a reflecting inner surface.

10. The method according to claim 9, wherein radiation from said source of non-visible radiation is directed through the table of the gemstone while the gemstone is in its setting.

11. Apparatus for identifying a gemstone, particularly a diamond, comprising:
    exciting means for exciting the gemstone to cause it to emit luminescence radiation according to a luminescence spectrum unique to the respective gemstone, in which the light intensity uniquely varies as a function of wavelength;
    light-distributing means for uniformly distributing the luminescence radiation;
    a light-measuring system for measuring the level of the uniformly-distributed luminescence radiation at each of a plurality of preselected wavelengths of its luminescence spectrum;
    and display means for displaying a value representing the level of the luminescence radiation at the preselected wavelengths to identify the respective gemstone and to distinguish it from other gemstones.

12. The apparatus according to claim 11, wherein the luminescence radiation of the gemstone is measured at least at six preselected wavelengths of its luminescence spectrum.

13. The apparatus according to claim 11, wherein said light-measuring system includes a plurality of detectors each sensitive to a different frequency band of the spectrum.

14. The apparatus according to claim 11, wherein said exciting means comprises a source of non-visible exciting radiation.

15. The apparatus according to claim 14, wherein said light-distributing means comprises a light-diffusing surface for uniformly distributing the luminescence radiation before it is measured by said measuring system.

16. The apparatus according to claim 15, wherein said light-diffusing surface is an integrating sphere.

17. The apparatus according to claim 15, wherein said light-measuring system includes at least one light detector detecting the light via a pinhole through said light-diffusing surface.

18. The apparatus according to claim 17, wherein said light-measuring system further includes a baffle shielding said pinhole and its detector from direct exposure to the source of non-visible radiation.

19. The apparatus according to claim 17, wherein the light-measuring system includes a plurality of light detectors each detecting the light via a pinhole through the light-diffusing surface, and a baffle for each pinhole shielding the pinhole and its detector from direct exposure to the source of non-visible radiation.

20. The apparatus according to claim 14, further including a window for passing the exciting radiation in one direction to the gemstone, and for passing the luminescence radiation in the opposite direction from the gemstone to the light-measuring system; and a mounting device for mounting the gemstone on one side of said window with the table of the gemstone facing the window.

21. The apparatus according to claim 20, wherein the gemstone at said one side of the window is enclosed by an enclosure having a highly reflective inner surface.

22. The apparatus according to claim 14, wherein said exciting means further comprises a filter for removing the visible radiation from the source of non-visible radiation before exposing the gemstone thereto.

23. The apparatus according to claim 14, wherein said exciting means further comprises a collimating lens for collimating the non-visible radiation before exposing the gemstone thereto.

* * * * *